United States Patent [19]

Burchill et al.

[11] Patent Number: 4,735,093

[45] Date of Patent: Apr. 5, 1988

[54] APPARATUS FOR APPLYING A LOAD TO A MATERIAL

[75] Inventors: Peter J. Burchill, Briar Hill; Richard H. Stacewicz, Maidstone; Stephen D. Boyd, Melton West; Cameron J. Stewart, Gisborne; John D. Thomas, Lower Templestowe, all of Australia

[73] Assignee: Commonwealth of Australia, Canberra, Australia

[21] Appl. No.: 900,763

[22] Filed: Aug. 26, 1986

[30] Foreign Application Priority Data

Aug. 27, 1985 [AU] Australia .............................. PH2157

[51] Int. Cl.$^4$ .............................................. G01N 3/20
[52] U.S. Cl. ...................................................... 73/854
[58] Field of Search ................. 73/849, 850, 851, 852, 73/853, 854, 805, 806; 364/508

[56] References Cited

U.S. PATENT DOCUMENTS

| | | |
|---|---|---|
| 2,479,984 | 8/1949 | Stock . |
| 3,500,679 | 7/1968 | Smith . |
| 3,808,880 | 5/1974 | Berman et al. ......................... 73/805 |
| 4,033,181 | 7/1977 | Oeser . |
| 4,314,482 | 2/1982 | Krainski, Jr. .......................... 73/805 |
| 4,574,356 | 3/1986 | Schattschneider et al. ......... 364/508 |

FOREIGN PATENT DOCUMENTS

| | | |
|---|---|---|
| 1798128 | 11/1971 | Fed. Rep. of Germany . |
| 623978 | 5/1949 | United Kingdom . |
| 644381 | 10/1950 | United Kingdom . |
| 1377607 | 11/1971 | United Kingdom . |
| 1408411 | 10/1975 | United Kingdom . |
| 2043266 | 10/1980 | United Kingdom . |
| 2055211 | 2/1981 | United Kingdom . |
| 344326 | 11/1977 | U.S.S.R. . |
| 326480 | 2/1979 | U.S.S.R. . |
| 748173 | 4/1979 | U.S.S.R. . |
| 896493 | 1/1982 | U.S.S.R. ............................... 73/849 |

Primary Examiner—Jerry W. Myracle
Attorney, Agent, or Firm—Roylance, Abrams, Berdo & Goodman

[57] ABSTRACT

A method of and an apparatus for applying 3 or 4 point bending to a specimen of a material. The apparatus comprises bending members to contact the specimen, a drive system coupled to at least one of the bending members to cause relative vertical movement between the bending members to deflect the specimen, and a microprocessor interfaced with the drive system to control the operation of the drive system in accordance with a computer programm. The method is characterized by controlled monitoring of the actual experimental conditions applied to the specimen and varying of the operation of the drive system when the actual experimental conditions diverge from the required experimental conditions.

8 Claims, 7 Drawing Sheets

FIG_1A_

FIG. 1B.

FIG_2B

APPARATUS FOR APPLYING A LOAD TO A MATERIAL

FIELD OF THE INVENTION

The present invention relates to a method of applying a load to a material, and in particular relates to a method of testing the mechanical properties of the material by applying a load to the material. The present invention also relates to apparatus for carrying out 3 or 4 point bending experiments on a specimen of a material.

BACKGROUND AND SUMMARY OF THE INVENTION

There are a number of situations such as in the mechanical testing of materials in which there is a need to apply a load to a material in a controlled manner.

According to the present invention there is provided a method of applying a load to a material comprising, positioning the material in a rig operable to apply the load, inputting data into a means to control the loading of the material, said data defining the required loading conditions, activating said control means to cause the material to be loaded, periodically determining the stress and/or strain applied to said material with sensor means associated with the rig, and varying the loading of the material by said control means in response to variations of the determined stress and/or strain from the input data.

The term "loading" as used herein is understood to means the application of a force to the material.

There is a wide range of apparatus capable of testing the mechanical properties of materials by a variety of experiments such as tensile, compression, fatigue and 3 or 4 point bending. The characteristic feature of these and other experiments used to investigate the properties of materials is that a load is applied to a specimen of the material and the response of the material to the load is measured over a period of time.

According to the present invention there is provided a method of testing the mechanical properties of a material by applying a load to the material comprising, positioning a specimen of the material in a test rig operable to apply a load to the specimen and thereby to deform or to deflect the specimen, inputting data into means to control the deformation or deflection of the specimen by the test rig, said data defining the experimental conditions for deforming or deflecting the specimen, activating said control means to cause said specimen to be deformed or deflected, periodically determining the stress and/or strain applied to the specimen as a consequence of the experimental conditions with sensor means associated with the specimen, and varying the control of the deformation or deflection of the specimen by said control means in response to variations of the determined stress and/or strain from the input data.

There are a number of known test rigs that are capable of carrying out a selection of different experiments to test the mechanical properties of a material. As indicated above, such experiments include tensile, compression, fatigue and 3 or 4 point bending carried out under constant stress, constant strain, variable stress or variable strain conditions.

A general disadvantage of the known multi-functional test rigs is that there is only limited access to the work station at which the specimen to be tested is positioned. As a consequence, it is difficult to carry out a visual inspection of the specimen during the course of an experiment, which often is useful in terms of assessing the changes occurring to the material as a consequence of the applied load. Furthermore, such limited access to the work piece prevents the positioning of equipment such as microscopes, photomultipliers and sound detection equipment in close proximity to the specimen to permit other experiments to be carried out simultaneously with the deformation of the specimen. A particular disadvantage of such multi-functional test rigs when set up to carry out 3 or 4 point bending experiments is that the under surface of the specimen is the tensile surface since the load is applied from above the specimen. As a consequence, it is not possible to carry out experiments to investigate the crazing characterisitcs of a plastics material since it is not possible to maintain a solvent in contact with the tensile surface.

According to the present invention there is provided an apparatus for carrying out 3 or 4 point bending experiments on a specimen of a material comprising, a work station comprising two outer bending members and either one or two intermediate bending members to support the specimen in a generally horizontal plane and to define the points of contact with the specimen for the 3 or 4 point bending experiments, a drive means to cause relative vertical movement between the two outer bending members and the or each intermediate bending member so that the upper surface of the specimen is the tensile surface.

It is preferred that the apparatus further comprise a frame to support the work station and the drive means, with the two outer bending members being coupled to the drive means and the or each intermediate bending member being connected to the frame.

It is also preferred that the apparatus comprise sensor means to detect the stress and/or strain applied to the specimen and display means to display the detected values of stress and/or strain.

With such an arrangement the work station may be positioned on an upper section of the support frame above the drive means so that there is generally unrestricted access to the tensile surface of the specimen, thereby permitting improved visual inspection of the specimen and simultaneous experiments based on the use of additional equipment conveniently and necessarily positioned in relation to the tensile surface of the specimen. Furthermore, with such an arrangement it is possible to carry out effective experiments to determine the crazing characteristics of a plastics material, since solvent can be maintained in contact with the tensile surface of the specimen.

BRIEF DESCRIPTION OF THE FIGURES OF THE DRAWING

A detailed description of the present invention is now provided with reference to the accompanying drawings in which:

FIGS. 1 and 2 (including parts 1A, 1B, 2A and 2B) are a flow chart for a preferred computer program to control the loading of a specimen in a 3 or 4 point bending experiment;

DETAILED DESCRIPTION OF THE PREFERRED EMBODIMENT

Figure 1A:
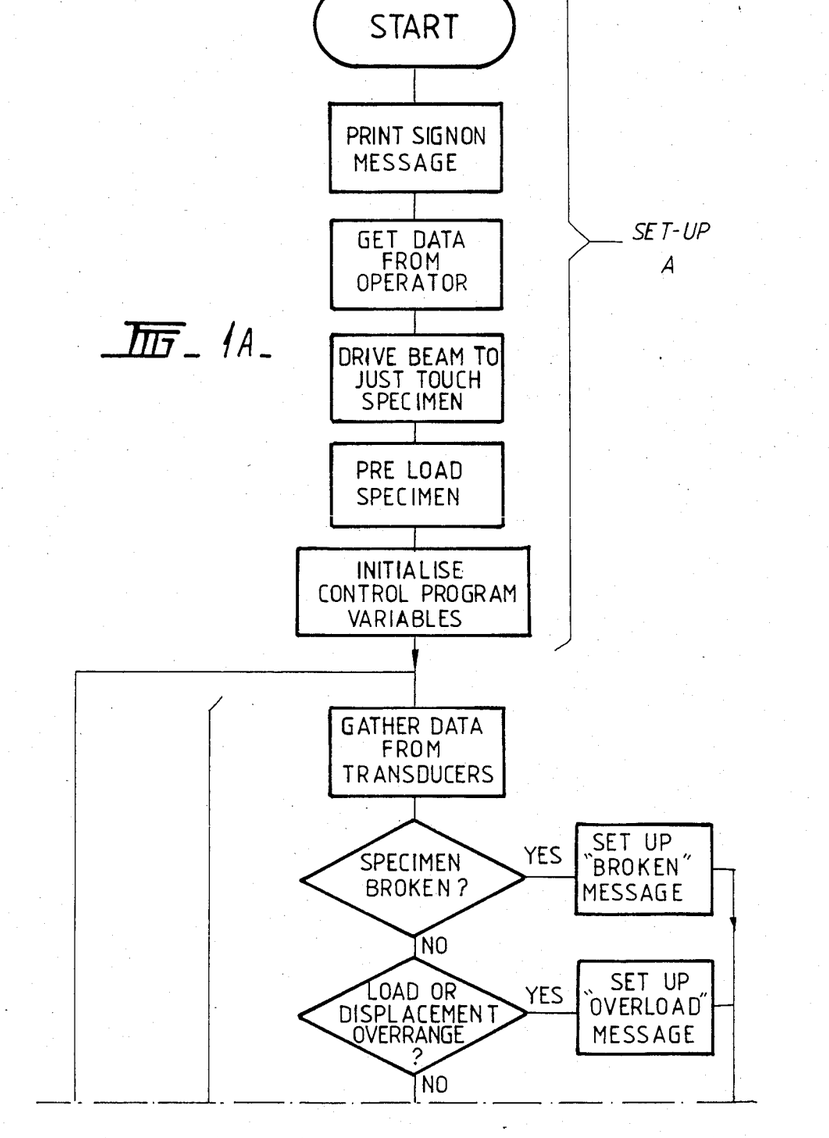
Figure 1B:
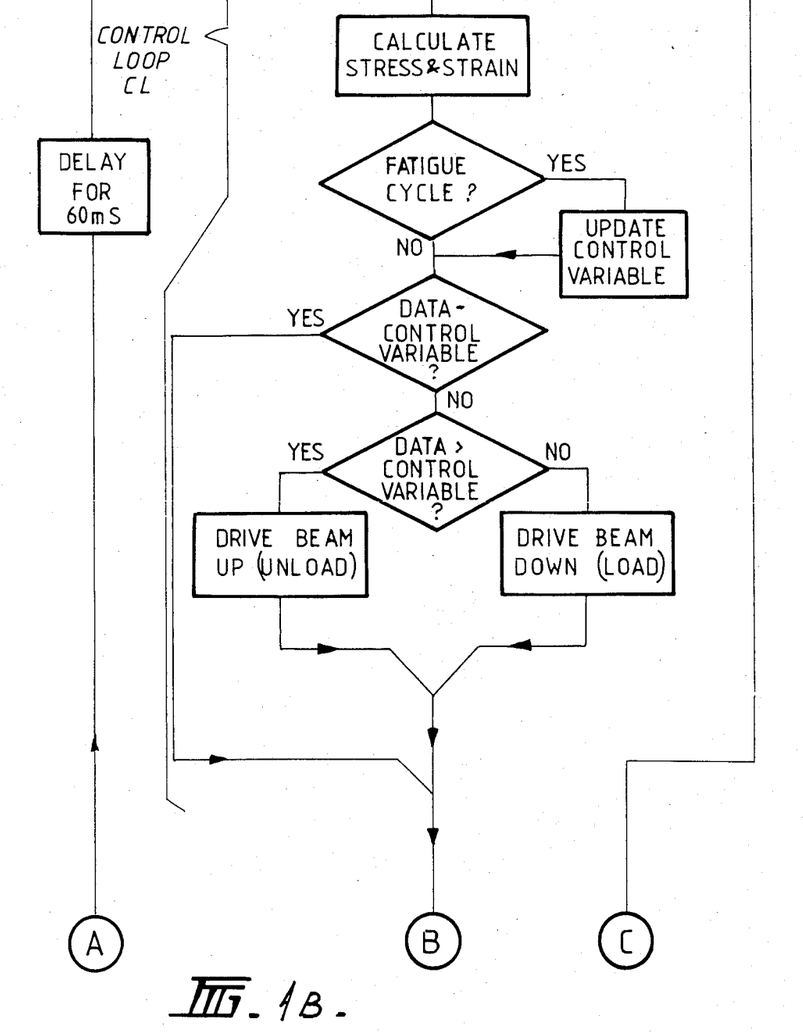
Figure 2A:
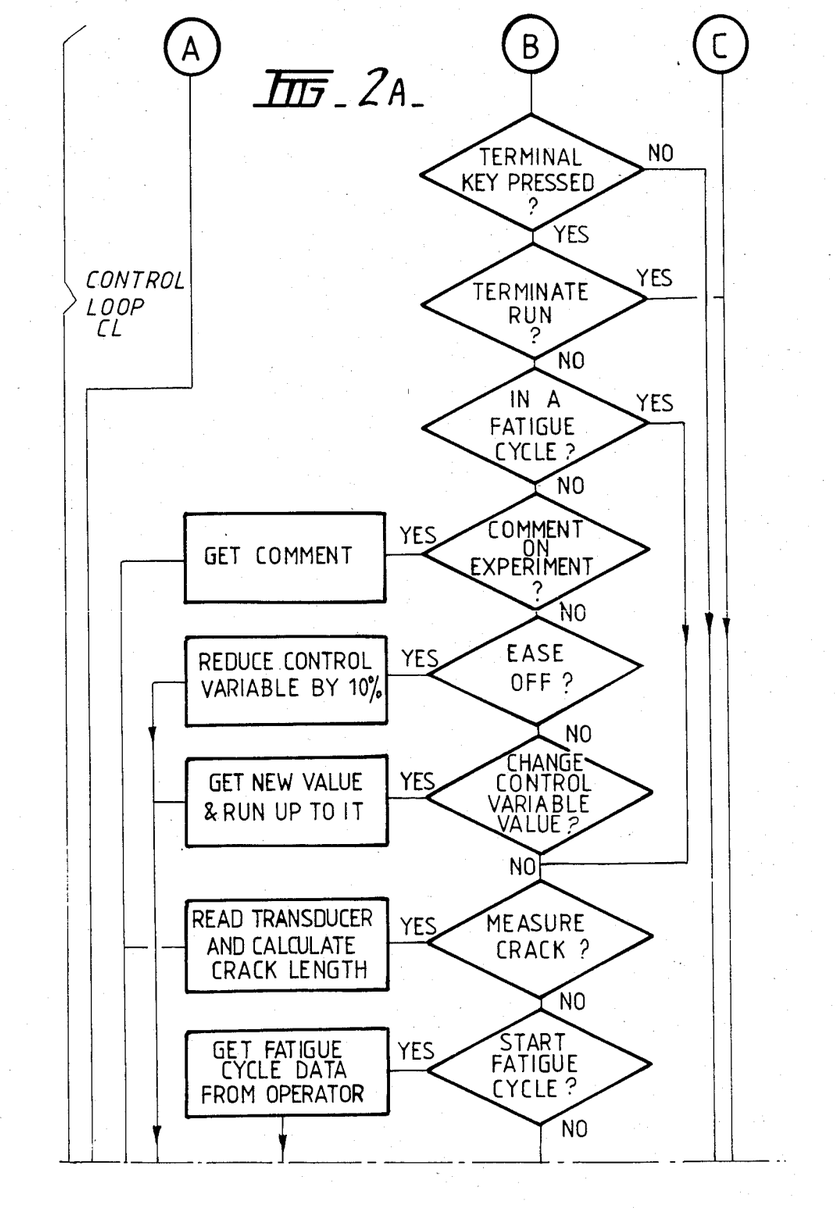
Figure 2B:
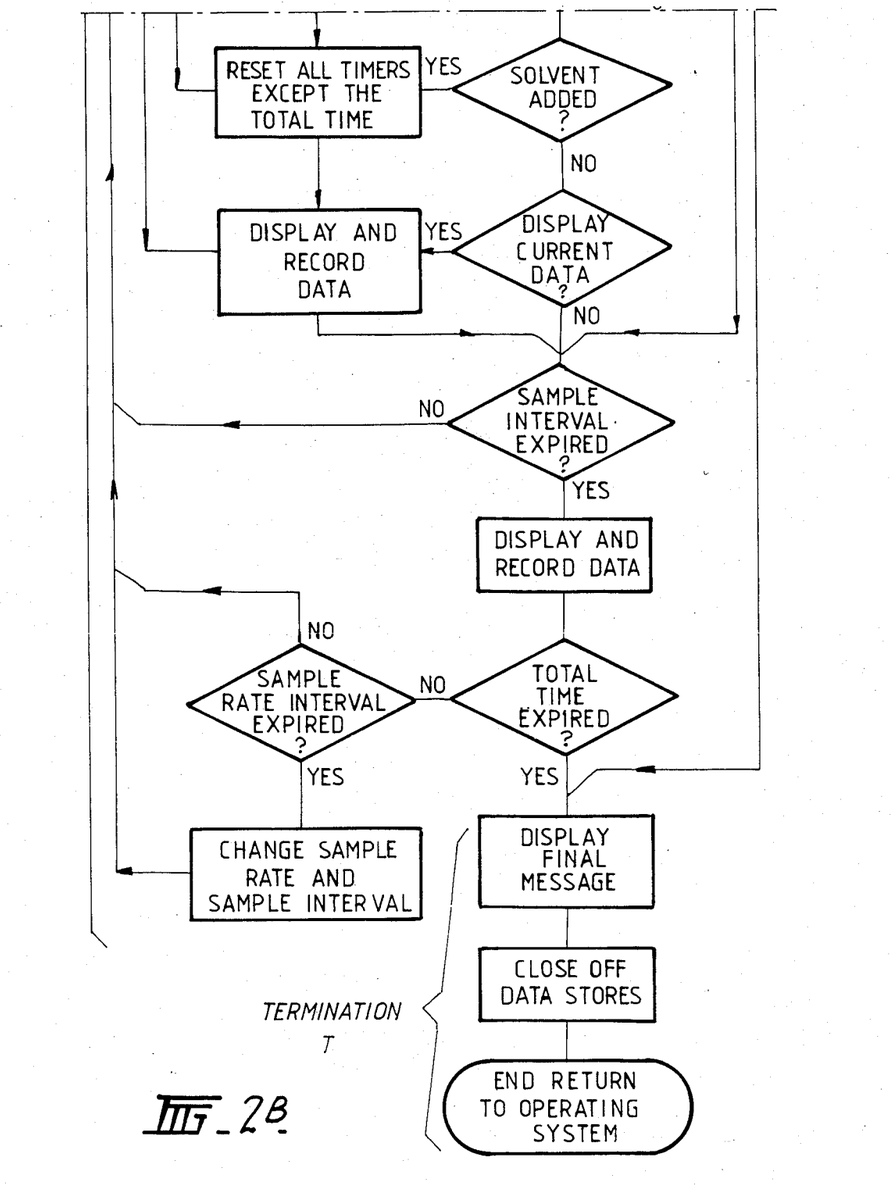

In FIGS. 1 and 2 is shown a flow chart for a computer program to control the loading of a specimen in a 3 or 4 point bending experiment in a test rig having bending members to contact the specimen, a drive means coupled to at least one of the bending members to cause relative vertical movement between the bending members thereby to deflect the specimen and a microprocessor interfaced with the drive means to control the operation of the drive means in accordance with the computer program. The test rig further comprises a sensor means to detect the load applied to and the displacement of the specimen during the course of the experiment and a display means to display the detected values of the stress and/or strain.

The computer program may conveniently be divided into the following three stages each of which comprises a number of steps: a set-up stage A; a control loop stage CL; and a termination stage T.

The set-up stage A involves the inputting of data into the microprocessor, the data comprising information concerning the specimen (such as the dimensions) and details of the experiment to be carried out. For example, if the experiment is to investigate the crazing characteristics of a plastics material, the input data will indicate that the control variable is stress or strain and nominate the value of the stress or strain to be applied to the specimen. On the other hand, if the experiment is to investigate the creep characteristics of a plastics material, the input data will indicate that the control variable is stress and nominate a selected stress to be applied to the specimen during the course of the experiment.

After the data has been entered into the microprocessor, the microprocessor activates the drive means to cause relative movement between the bending members so that a small load in the order of 0.5N is applied to the specimen. At this point, a clock in the microprocessor is activated and the microprocessor controls the drive means to load the specimen at a fixed preselected rate to the nominated stress or strain value.

The principal features of the control loop stage CL are;

(1) the processing of the values of load and/or displacement detected by the sensors (converted to stress and strain) to determine whether or not the experiment is proceeding in accordance with the preselected data, and, if necessary, the varying of the control of the operation of the drive means in response to variations of the detected data from the preselected data, and (2) the periodic display of the values of stress and/or strain and the permanent recording of the display.

The first series of steps in the control loop CL are concerned with item (1) above. The first step in this series is to gather data from the sensors associated with the test rig. The data is then assessed to determine whether or not the specimen is broken or the detected load or displacement is clearly out of the range of reasonable values that would be expected, in which case further processing on the data is not necessary and the experiment is terminated. The data that does not fall into these categories is then processed to calculate the stress and strain values, with such calculations being dependent on the input data comprising the dimensions of the specimen.

The next step in the control loop CL is an enquiry as to whether or not a fatigue experiment is being carried out, in which case it would be necessary to up-date the control variable in accordance with the input data.

The detected values of stress and/or strain are compared with the selected control variable in the input data to determine whether or not the detected values of stress and/or strain are equal to, greater than or less than the control variable. In the event that the detected stress and/or strain is *not* equal to the control variable the microprocessor activates the drive means to reposition the bending members so that the stress and/or strain applied to the specimen equals the control variable.

The next step in the control loop CL is an enquiry as to whether or not a terminal key has been pressed. If the answer to the enquiry is YES the program carries out a check to locate the terminal key that has been pressed and then responds to the particular enquiry or instruction at the terminal key. A selection of terminal keys is shown in FIG. 2, although it would be understood by a person skilled in the art that the number and type of terminal keys is not limited to the array shown.

The final series of steps in the control loop CL are concerned with item (2) above, namely the display and permanent recording of data. The series of steps comprises "SAMPLE INTERVAL EXPIRED?", "DISPLAY AND RECORD DATA", "TOTAL TIME EXPIRED?", "SAMPLE RATE INTERVAL EXPIRED?" and "CHANGE SAMPLE RATE AND SAMPLE INTERVAL".

The step "SAMPLE INTERVAL EXPIRED?" is an enquiry as to whether or not a pre-selected time interval has elapsed since the previous display and permanent recording of values of stress and strain.

The step "SAMPLE: RATE INTERVAL EXPIRED?" is an enquiry as to whether or not the pre-selected time during which the values of stress and strain are to be displayed and recorded in permanent form at any given sample interval has elapsed.

The final series of steps in the control loop CL reflects the flexibility of the computer programme in that, whilst it is possible to monitor continuously the load and displacement detected by the sensors and therefore ensure that the test rig is controlled to operate in accordance with the input data, the program enables the timing of the display and recording of values of the calculated stress and strain to be varied as required. For example, in an experiment set to run for several weeks it may be desirable to obtain a permanent record of the values of stress and strain at short time intervals during the first day and in the remainder of the experiment it may only be necessary to record the values at longer time intervals. The program allows the sample rate and interval to be pre-selected to suit a particular experiment and also allows the operator to activate manually the display and recording of the values which may be desirable, for example, if a visual inspection of the specimen indicates that crazing is occurring. Furthermore, the program allows the pre-selected sample rate and interval to be varied by the operator during the course of the experiment.

With the above in mind, as is shown in FIG. 2, the final series of steps in the control loop CL comprises a sequence of enquiries to determine whether the timing of the detected data is significant in terms of the preselected sample rates and intervals and thus should be displayed and recorded in a permanent form.

The following steps in the computer program comprise the termination steps T.

It can be appreciated that the above computer program allows either stress or strain control in the loading of the specimen. In this way the specimen may be bent at a prescribed load or deflection and this status can be maintained until a further change is desired. Values of stress and strain and other experimental measurements can be recorded onto a flexible diskette and printed at selected time intervals, or as required by the operator.

The computer program can also provide for the control of fatigue experiments with the fatigue cycles imposed as a combination of ramps and plateaus. The number of fatigue cycles can be preselected, and started and finished at preselected control limits, or fatigue cycling can continue until terminated by the operator. Values of stress and strain can be recorded at selected time intervals for the limits of the cycle, and for example, cycling rates of up to 1 Hz may be selected.

It can readily be appreciated that the output data displayed and recorded in permanent form is not limited to stress and strain and could include the output of other external equipment that may be placed in close proximity to the specimen to carry out simultaneous experiments. For example, the kinetics of crack and craze growth in plastics materials is of fundamental importance to their use in load bearing applications. By using a traveling microscope or video microscaler with a digital output the length of a crack or craze can be recorded against time with the values of stress and strain.

Figure 3:
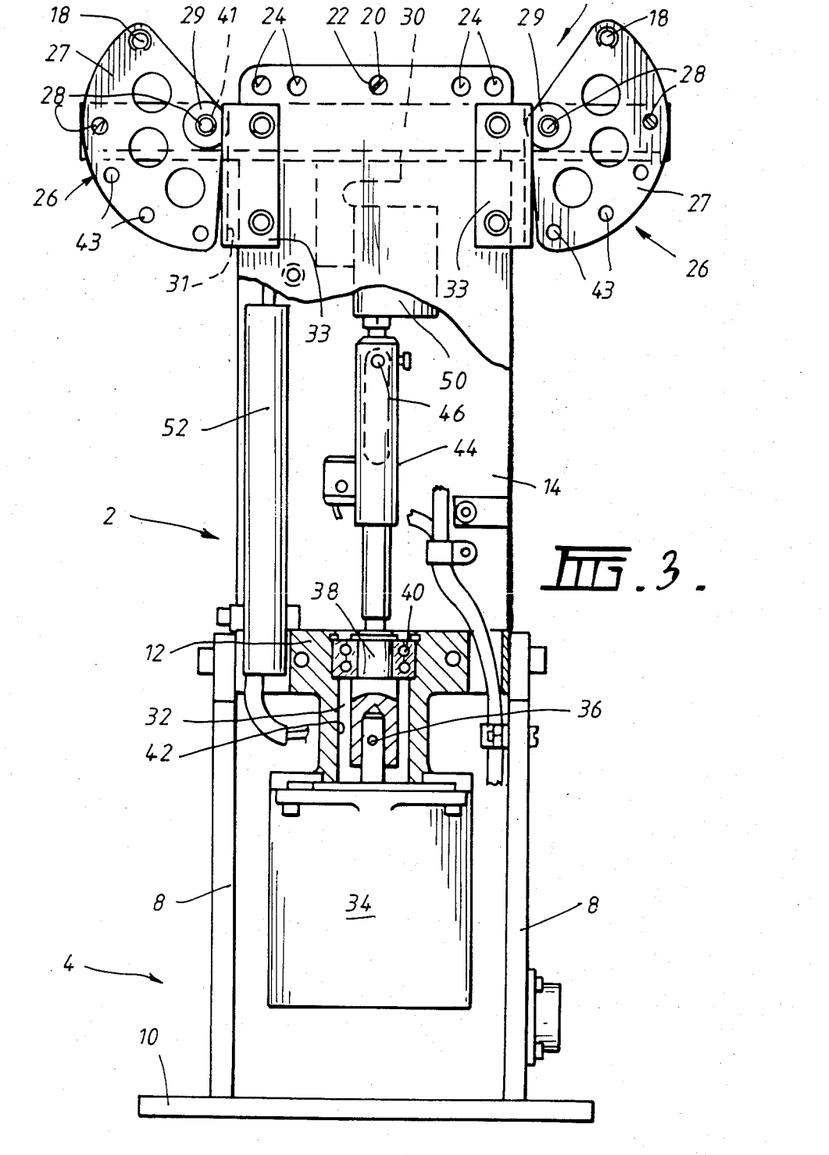
FIG. 3 is a partially cut-away, partially sectional front elevation of a preferred embodiment of an apparatus for carrying out 3 or 4 point bending experiments.
Figure 4:
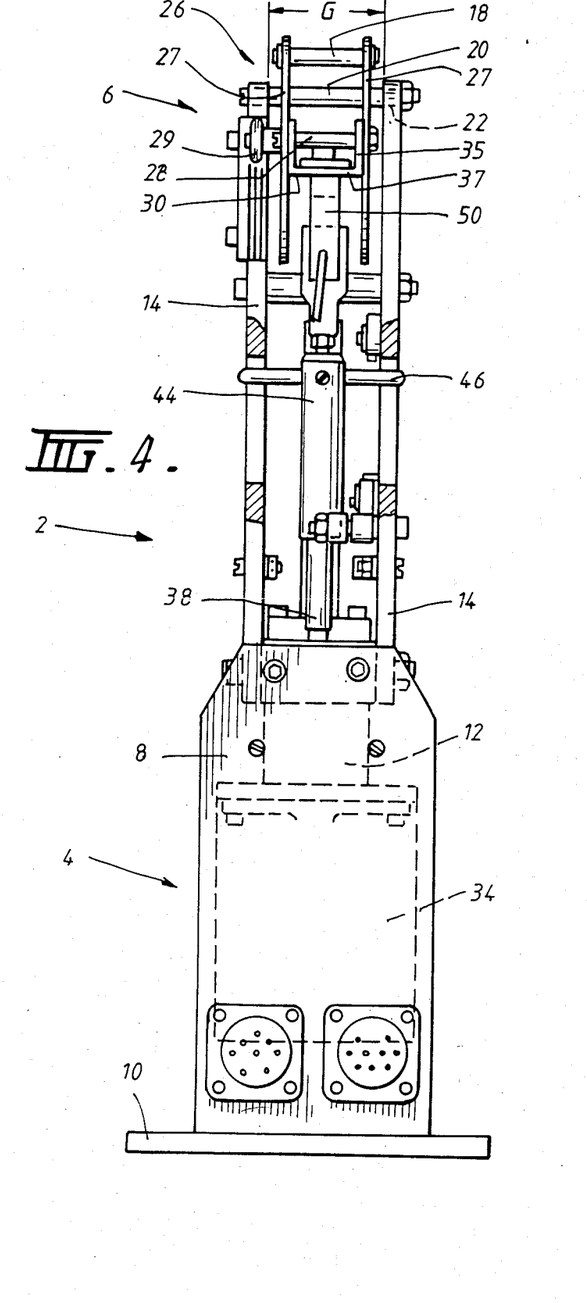
FIG. 4 is a side elevation of the apparatus shown in FIG. 3.
Figure 5:
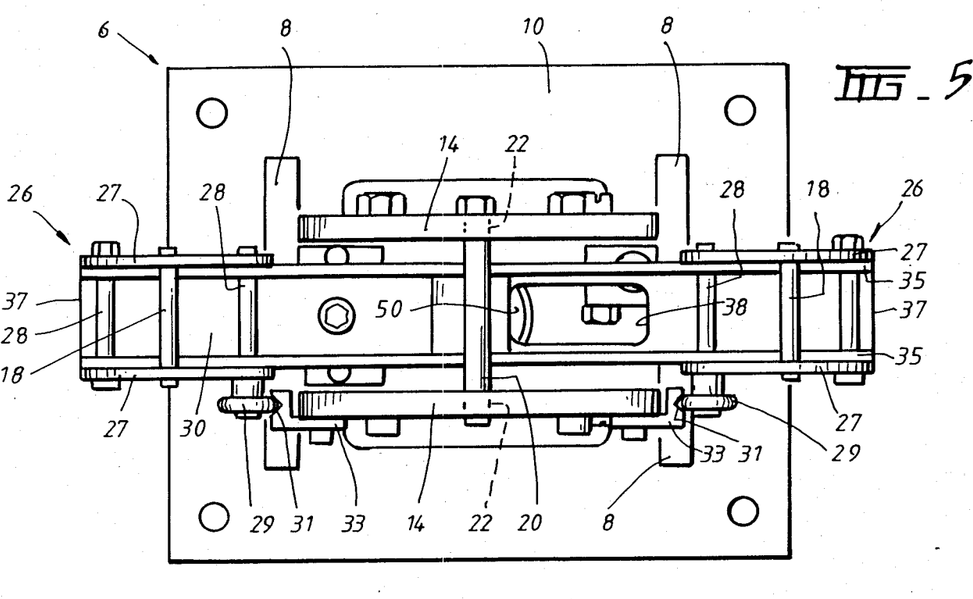
FIG. 5 is a plan view of the apparatus shown in FIGS. 3 and 4.

A preferred embodiment of a 3 or 4 bending apparatus in accordance with the invention is shown in FIGS. 3 to 5.

The bending apparatus 2 shown comprises a support frame 2, a drive means 4 and a work station 6 at which a specimen to be tested is supported for bending in a 3 or 4 point bending experiment.

The support frame 2 comprises a pair of spaced apart upright parallel lower support plates 8 secured to a base plate 10, a mounting block 12 extending between and connected to the upper end sections of the support plates 8, and a pair of parallel upright upper support plates 14 connected to and extending upwardly from the mounting block 12. As can best be seen in FIG. 4 the upper support plates 14 are spaced apart to define a gap G therebetween.

The work station 6 comprises two outer bending members 18 and one central bending member 20 arranged so that in use the bending members contact and support the respective upper and lower surfaces of a generally rectangular specimen of a material to be tested in a 3 point bending experiment.

The central bending member 20 is positioned to extend across the gap G between the upper support plates 14 and is received in aligned openings 22 (FIG. 3) in the upper support plates 14, and thus is fixed to the support frame 2. The upper support plates 14 are provided with additional aligned openings 24 to allow the central bending member 20 to be re-positioned with another bending member (not shown) so that the apparatus can carry out a 4 point bending experiment.

The outer bending members 18 are coupled to the drive means 4 and can be displaced vertically by the drive means 4, as will be described hereinafter.

As can best be seen in FIG. 5, each outer bending member 18 is connected to a yoke 26, and each yoke 26 is connected to opposite ends of a mounting beam 30 positioned to extend through the gap G between the upper support plates 14 and below the central bending member 20. Each yoke 26 comprises two spaced apart parallel plates 27 connected together by a pair of pins 28. Each plate has a curved outer edge and two straight edges that converge to an apex. The plates have aligned apertures 41 in the region of the apices and aligned apertures 43 at spaced intervals in the region of the curved edges. The mounting beam 30 is a channel section having two side walls 35 extending from a central web 37. The central web 37 is positioned to extend generally horizontally and has a rectangular cut-out section 38. The side walls have aligned apertures at each end. The pins 28 are positioned to extend through these apertures and the apertures 41, 43 in the plates 27 hereby to connect the yokes 26 to the mounting beam 30. The provision of a plurality of the apertures 43 around the region of the curved outer edge of the plates 27 means that the orientation of the yokes 26 with respect to the mounting beam 30 can be changed, thereby to vary the vertical displacement of the outer bending members 18 from the central bending member 20 so that the apparatus can receive specimens having a range of thicknesses.

As can best be seen in FIG. 5, a roller 29 is connected to the inner one of each pair of pins 28. The rollers 29 are positioned to travel in a grooves 31 formed in guide plates 33 attached to the upper support plates 14. The rollers 29 and guide plates 33 define a self-centering mechanism for the work station 6.

As can best be seen in FIG. 3, the drive means 4 comprises a stepping-up motor 34 connected to the mounting block 12 and extending into the space between the lower support plates 8. A drive shaft 36 extends from the stepping-up motor into a central bore 32 in the mounting block 12. A spindle 38 is connected at one end to the drive shaft 36 and is supported for rotation about its axis by bearings 40 positioned in the annular gap between the spindle 38 and the inner wall 42 of the bore 32.

The other end of the spindle 38 is threaded and extends into an internally threaded spindle nut 44. A pair of pins 46 (FIG. 4) are connected to and extend from opposite sides of the spindle nut 44 into vertically extending slots (not shown) formed in the upper support plates 14, thereby preventing rotation of the spindle nut 44 relative to the support frame 2.

A load cell 50 connects the spindle nut 44 to the mounting beam 30, and thereby completes the coupling between the outer bending members 18 and the drive means 4.

The apparatus further includes a transducer 52 to measure the displacement of the specimen during a 3 or 4 point bending experiment.

In use, with the work station set-up for a 3 point bending experiment, a rectangular specimen of a material to be tested is positioned to rest on the central bending member 20 with the outer bending members 18 bearing against the upper surface of the specimen.

The stepping-up motor 34 is then operated to cause the spindle 38 to rotate within the spindle nut 44, thereby moving the mounting beam 30, yokes 26 and outer bending members 18 downwardly and causing bending of the specimen about the central bending member 20. Measurements of the load and displacement during the course of the experiment are detected by the load cell 50 and the displacement transducer 52, and may be recorded by any suitable apparatus and display means (not shown).

It can readily be appreciated that the above apparatus 2 is such that there is generally unrestricted access to the specimen from above, with the consequence that it is possible to inspect visually the specimen during the course of the experiment, as well as to position other equipment in relation to the specimen so as to permit simultaneous experiments to be carried out. Furthermore, it can readily be appreciated that by forming the work station so that the upper surface of the specimen is the tensile surface, it is possible to carry out crazing experiments in relation to the specimen.

It can also be readily appreciated that the computer program described in relation to FIGS. 1 and 2 could be interfaced with the drive means to control the operation of the apparatus.

We claim:

1. An apparatus for carrying out 3 point bending experiments on a specimen of a material comprising, a work station comprising two outer bending members and one intermediate bending member to support the specimen in a generally horizontal plane and to define the points of contact with the specimen for the 3 point bending experiments, a drive means to cause relative vertical movement between the two outer bending members and the intermediate bending member so that the upper surface of the specimen is the tensile surface, a frame to support the work station and the drive means; with the two outer bending members coupled to one of the drive means and the frame, and the intermediate bending member coupled to the other of the drive means and the frame; a sensor means to detect the load applied to and the displacement of the specimen, and a microprocessor interface with the drive means to control the operation of the drive means.

2. The apparatus as claimed in claim 1, wherein the microprocessor is coupled to the sensor means and is operable to convert the detected values of load and displacement to values of stress and strain and is responsive to the values of stress and strain thereby to control the operation of the drive means.

3. The apparatus as claimed in claim 1, wherein the outer bending members are coupled to the drive means and the intermediate bending member is coupled to the frame, and the drive means and the microprocessor are located with respect to the work station to permit generally unrestricted access to the upper surface of the specimen.

4. The apparatus as claimed in claim 3, said apparatus further comprising means to center the work station.

5. An apparatus for carrying out 4 point bending experiments on a specimen of a material comprising, a work station comprising two outer bending members and two intermediate bending members to support the specimen in a generally horizontal plane and to define the points of contact with the specimen for the 4 point bending experiments, a drive means to cause relative vertical movement between the two outer bending members and the intermediate bending members so that the upper surface of the specimen is the tensile surface, a frame to support the work station and the drive means; with the two outer bending members coupled to one of the drive means and the frame, and the intermediate bending members connected to the other of the drive means and the frame; a sensor means to detect the load applied to and the displacement of the specimen, and a microprocessor interfaced with the drive means to control the operation of the drive means.

6. The apparatus as claimed in claim 5, wherein the microprocessor is coupled to the sensor means and is operable to convert the detected values of load and displacement to values of stress and strain and is responsive to the values of stress and strain thereby to control the operation of the drive means.

7. The apparatus as claimed in claim 5, wherein the outer bending members are coupled to the drive means and the intermediate bending members are coupled to the frame, and the drive means and the microprocessor are located with respect to the work station to permit generally unrestricted access to the upper surface of the specimen.

8. The apparatus as claimed in claim 7, said apparatus further comprising means to center the work station.

* * * * *